(12) United States Patent
Dilk et al.

(10) Patent No.: US 10,415,001 B2
(45) Date of Patent: Sep. 17, 2019

(54) DERIVATIVES OF 1-(4-METHYLCYCLOHEXYL)-ETHANOLS

(71) Applicant: Symrise AG, Holzminden (DE)

(72) Inventors: Erich Dilk, Holzminden (DE); Edison Diaz, Goslar (DE); Pierre Kurzenne, Bois Colombes (DE); Walter Kuhn, Holzminden (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 15/197,199

(22) Filed: Jun. 29, 2016

(65) Prior Publication Data
US 2017/0002294 A1    Jan. 5, 2017

(30) Foreign Application Priority Data

Jun. 30, 2015 (EP) .................................... 15174508

(51) Int. Cl.
| | |
|---|---|
| *A61K 8/18* | (2006.01) |
| *C11B 9/00* | (2006.01) |
| *C07C 69/24* | (2006.01) |
| *A61K 8/04* | (2006.01) |
| *A61K 8/33* | (2006.01) |
| *A61K 8/37* | (2006.01) |
| *A61Q 19/10* | (2006.01) |
| *C07C 43/115* | (2006.01) |
| *C07C 43/162* | (2006.01) |
| *C07C 69/02* | (2006.01) |
| *C07C 69/675* | (2006.01) |
| *C07C 69/68* | (2006.01) |

(52) U.S. Cl.
CPC ............ *C11B 9/0034* (2013.01); *A61K 8/042* (2013.01); *A61K 8/33* (2013.01); *A61K 8/37* (2013.01); *A61Q 19/10* (2013.01); *C07C 43/115* (2013.01); *C07C 43/162* (2013.01); *C07C 69/02* (2013.01); *C07C 69/24* (2013.01); *C07C 69/675* (2013.01); *C07C 69/68* (2013.01); *C07C 2101/14* (2013.01)

(58) Field of Classification Search
CPC ....... C11B 9/0034; C11B 9/0015; A61K 8/33; C07C 43/115; C07C 69/02; C07C 69/24
See application file for complete search history.

(56) References Cited

U.S. PATENT DOCUMENTS 4,622,221 A * 11/1986 Schleppnik .............. A61K 8/37
424/45

FOREIGN PATENT DOCUMENTS

| DE | 2650602 | | 5/1977 |
|---|---|---|---|
| EP | 2281581 | | 2/2011 |
| GB | 1545561 | * | 5/1979 |

OTHER PUBLICATIONS

European Search Report for European Application No. EP 15174508. 0, Completed by the European Patent Office, dated Oct. 28, 2015, 4 Pages.

* cited by examiner

*Primary Examiner* — John R Hardee
(74) *Attorney, Agent, or Firm* — Brooks Kushman P.C.

(57) ABSTRACT

The invention relates to mixtures having:
components (a) having at least one fragrance of the formula (I)

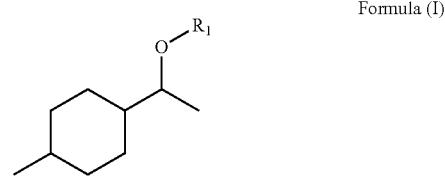

Formula (I)

where
R1=OC—R2, CH$_2$OR3, C1-C8 open-chain or branched aliphatic radical, optionally substituted and/or unsaturated,
with R2=an open-chain or branched aliphatic radical, optionally substituted and/or unsaturated, having 2-10 C atoms,
with R3=an open-chain or branched aliphatic radical, optionally substituted and/or unsaturated, having 1-8 C atoms, and
components (b) having at least one fragrance, different from the fragrances of component a,
characterized in that the weight ratio of all components (a) to all components (b) is from 1:10 to 1:10000.

17 Claims, No Drawings

DERIVATIVES OF 1-(4-METHYLCYCLOHEXYL)-ETHANOLS

CROSS-REFERENCE TO RELATED APPLICATIONS

This application claims foreign priority benefits under 35 U.S.C. § 119(a)-(d) to European patent application number EP 15174508.0, filed Jun. 30, 2015, which is incorporated by reference in its entirety.

TECHNICAL FIELD

The present invention relates to the field of fragrances.

BACKGROUND

DE2650602 A1 discloses a structural space which encompasses derivatives of 1-(4-methylcyclohexyl)ethanol as well as derivatives of many other compounds, with compounds within the structural space being used against unpleasant odours (deodorants). The compounds alleviate the offensive effect of a malodorous substance or of a malodour on the human sense of smell, without this effect relating to any particular mechanism. For the explicitly stated derivatives of 1-(4-methylcyclohexyl)ethanol from examples 25 and 26, no odour at all is reported. Moreover, it is shown in the examples that compounds 25 and 26 are able to diminish the odour of bad odours, to the point of a clean odour.

SUMMARY

It is an object of the invention to provide compositions for boosting pleasing odours.

DETAILED DESCRIPTION

The object is achieved by means of a mixture comprising
a) at least one fragrance of the formula (I)

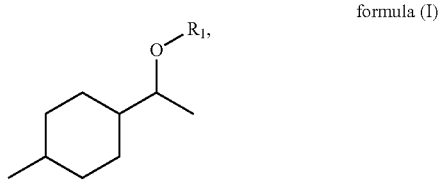

formula (I)

where
R1=OC—R2, CH2OR3, C1-C8 open-chain or branched aliphatic radical, optionally substituted and/or unsaturated,
with R2=an open-chain or branched aliphatic radical, optionally substituted and/or unsaturated, having 2-10 C atoms,
with R3=an open-chain or branched aliphatic radical, optionally substituted and/or unsaturated, having 1-8 C atoms,
b) at least one fragrance, different from the fragrances of component a,
characterized in that the weight ratio of all components a to all components b is from 1:10 to 1:10000.

On the basis of the cited prior art it is surprising that these mixtures are able to boost pleasing odours, since the compounds of the general structural space from DE2650602 A1 are used in order to diminish odours, in other words to bring about exactly the opposite of the object of the present invention.

The compounds of the formula (I) may in particular comprise as radical R1 a propanoyl, butanoyl, 2-methylpropanoyl, 2-hydroxypropanoyl, methoxyethyl or 2-methylbut-2-enyl radical.

The mixture may comprise at least two fragrances of the formula (I).

In particular the compounds of the formula (I) may be one or more of the compounds listed below in Table 1.

The fragrances stated in Table 1 themselves possess predominantly flowery and fruity odour qualities and can therefore also themselves be used as fragrances, especially for generating flowery and fruity odour notes. In addition to their intrinsic odour, the fragrances are able to boost pleasing odours, with a boosting effect in particular on pleasing flowery and/or fruity odours. The pleasing odours, especially the pleasing flowery and/or fruity odours, may be boosted synergistically.

Certain compounds of the formula (I) are new; it is assumed that the compounds 1, 4, 5 and 6 from Table 1 are new.

TABLE 1

| | Formula | Name | Odorous description |
|---|---|---|---|
| 1 | | 1-(4-Methylcyclohexyl)ethyl propionate | Rose Geranyl Neryl Lychee |
| 2 | | 1-(4-Methylcyclohexyl)ethyl butyrate | Rose Blossom Carbinol Peach |

TABLE 1-continued

| | Formula | Name | Odorous description |
|---|---|---|---|
| 3 | | 1-(4-Methylcyclo-hexyl)ethyl isobutyrate | Rose Blossom |
| 4 | | 1-(4-Methylcyclo-hexyl)ethyl 2-hydroxy-propionate | Violet Lily Green |
| 5 | | 1-[1-Ethoxy-methoxy]ethyl]-4-methylcyclohexane | Green apple Lily of the valley |
| 6 | | 1-Methyl-4-[1-(3-methylbut-2-enoxy)ethyl]cyclohexane | Flowery, fruity |

Examples of the further at least one fragrance (component b) are found for example in S. Arctander, Perfume and Flavor Materials, Vol. I and II, Montclair, N.J., 1969, publication by author, or H. Surburg and J. Panten, Common Fragrance and Flavor Materials, 5th Ed., Wiley-VCH, Weinheim 2006.

The further at least one fragrance (component b) may for example be:

One or more extracts from natural raw materials such as essential oils, concretes, absolutes, resins, resinoids, balsams, tinctures such as e.g.

ambergris tincture; amyris oil; angelica seed oil; angelica root oil; aniseed oil; valerian oil; basil oil; tree moss absolute; bay oil; mugwort oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassia absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; Eau de brouts absolute; oak moss absolute; elemi oil; tarragon oil; Eucalyptus *citriodora* oil; eucalyptus oil; fennel oil; spruce needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; camomile oil blue; roman camomile oil; carrot seed oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; *Litsea cubeba* oil; laurel leaf oil; mace oil; marjoram oil; mandarin oil; massoia bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange blossom absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; styrax oil; tagetes oil; fir needle oil; tea tree oil; turpentine oil; thyme oil; tolu balsam; tonka absolute; tuberose absolute; vanilla extract; violet leaf absolute; verbena oil; vetiver oil; juniper berry oil; wine lees oil; wormwood oil; winter green oil; ylang ylang oil; hyssop oil; civet absolute; cinnamon leaf oil; cinnamon bark oil, and fractions thereof, or ingredients isolated therefrom;

individual odorants and/or mixtures from the following groups:

group of the hydrocarbons, such as e.g. 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

of the aliphatic alcohols such as e.g.

hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4- methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethylacetal; 1,1-dimethoxy-2,2,5-trimethyl-4-hexene; citronellyloxyacetaldehyde;

of the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

of the aliphatic sulphur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of the aliphatic nitriles such as e.g. 2-nonenenitrile; 2-tridecenenitrile; 2,12-tridecadienenitrile; 3,7-dimethyl-2,6-octadienenitrile; 3,7-dimethyl-6-octenenitrile;

of the aliphatic carboxylic acids and esters thereof such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynate; methyl 2-nonynate; allyl 2-isoamyloxy acetate; methyl 3,7-dimethyl-2,6-octadienoate;

of the acyclic terpene alcohols such as e.g. citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

of the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; and also the dimethyl- and diethylacetals of geranial, neral and 7-hydroxy-3,7-dimethyloctanal;

of the cyclic terpene alcohols such as e.g. menthol; isopulegol; α-terpineol; terpineol-4; menthan-8-ol; menthan-1-ol; menthan-7-ol; borneol; isoborneol; linalool oxide; nopol; cedrol; ambrinol; vetiverol; guaiol; and the formates, acetates, propionates, isobutyrates, butyrates, isovalerates, pentanoates, hexanoates, crotonates, tiglinates and 3-methyl-2-butenoates thereof;

of the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedar wood oil (methyl cedryl ketone);

of the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of the cycloaliphatic alcohols such as e.g. alpha,3,3-trimethylcyclohexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of the cyclic and cycloaliphatic ethers such as e.g. cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

of the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

of the cycloaliphatic aldehydes such as e.g. 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of the cycloaliphatic ketones such as e.g. 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

of the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of the esters of cycloaliphatic carboxylic acids such as e.g. allyl 3-cyclohexylpropionate; allyl cyclohexyloxyacetate; cis and trans-methyl dihydrojasmonate; cis and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

of the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3- phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropyl-phenyl)ethanol;

of the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha, alpha-dimethylphenylethyl acetate; alpha, alpha-dimethylphenylethyl butyrate; cinnamyl acetate; 2-phenoxyethyl isobutyrate; 4-methoxybenzyl acetate;

of the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

of the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropyl-phenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexyl-cinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxy-phenyl)propanal;

of the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenyl ethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenonitrile; 5-phenyl-3-methylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Mixtures according to the invention or compounds of the formula (I) may be used in liquid form, undiluted, or diluted with a solvent. Examples of suitable solvents for this purpose include ethanol, isopropanol, diethylene glycol monoethyl ether, glycerol, propylene glycol, 1,2-butylene glycol, dipropylene glycol, diethyl phthalate, triethyl citrate, isopropyl myristate. The solvents stated are very suitable indeed for dissolving the mixtures according to the invention or the compounds of the formula (I).

Furthermore, the mixtures according to the invention or the compounds of the formula I may be adsorbed on a carrier substance which ensures both fine division of the odorants in the product and controlled release in the application. Carriers of this kind may be porous inorganic materials such as light sulphate, silica gels, zeolites, gypsums, clays, clay granules, aerated concrete, and so on, or organic materials such as woods and cellulose-based substances.

The mixtures according to the invention or compounds of the formula I may also be present in microencapsulated form, in spray-dried form, as inclusion complexes or as extrusion products, and may be added in this form to the product to be perfumed. The properties of these forms of presentation of the mixtures according to the invention or compounds of the formula (I) may optionally be optimized further by "coating" with suitable materials in respect of more targeted fragrance release, preference being given for this purpose to the use of waxlike plastics such as polyvinyl alcohol, for example.

The microencapsulation may take place for example by the method known as coacervation, with the aid of capsule materials made, for example, of polyurethane-like substances or soft gelatins. Spray-dried products may be produced, for example, by the spray-drying of an emulsion, or dispersion, with the possible use of modified starches, proteins, dextrin and vegetable gums as carrier substances. Inclusion complexes may be produced, for example, by mixing the mixtures according to the invention or compounds of the formula I with cyclodextrins or urea derivatives in a suitable solvent, e.g. water. Extrusion products can be produced by melting the mixtures according to the invention or compounds of the formula I with a suitable waxlike substance and by extrusion with subsequent solidification, optionally in a suitable solvent, e.g. isopropanol.

Consumer products are, for example, perfumes, body care products, such as soaps, shower gels, shampoos, bath products, skin creams, body lotions and deodorants, and cleaning or care products for household use, such as laundry detergents, fabric softeners, room air improvers and cleaners. Further examples of consumer products are given below.

The mixtures according to the invention or the compounds of the formula (I) are very suitable indeed for use in a multiplicity of consumer products, and can be used, for example, in concentrated form, in solutions or in a modified form as described above. They are suitable for producing a very wide variety of consumer products, as for example of perfume extracts, eau de parfums, eau de toilettes, after-shaves, eau de colognes, pre-shave products, splash colognes and perfumed freshening wipes, and also for the perfuming of acidic, alkaline and neutral cleaners, such as floor cleaners, window cleaners, dishwashing detergents, bath and sanitary cleaners, scouring milk, solid and liquid toilet cleaners, carpet cleaners in powder and foam form, liquid detergents, powder detergents, laundry pretreatment products such as bleaches, soaking compositions and stain removers, fabric softeners, washing soaps, washing tablets, disinfectants, surface disinfectants, and air fresheners in liquid or gel-like form or in a form applied to a solid carrier, aerosol sprays, waxes and polishes such as furniture polishes, floor waxes, shoe creams, and also body care products such as, for example, solid and liquid soaps, shower gels, shampoos, shaving soaps, shaving foams, bath oils, cosmetic emulsions of the oil-in-water, water-in-oil and water-in-oil-in-water types such as, for example, skin creams and skin lotions, face creams and face lotions, sun protection creams and lotions, after-sun creams and lotions, hand creams and lotions, foot creams and lotions, hair removal creams and lotions, after-shave creams and lotions, tanning creams and lotions, hair care products such as, for example, hair sprays, hair gels, solid hair lotions, hair rinses, permanent and semi-permanent hair colorants, hair shaping compositions such as cold waves and hair straightening compositions, hair tonics, hair creams and hair lotions, deodorants and antiperspirants such as, for example, underarm sprays, roll-ons, deodorant sticks, deodorant creams, products of decorative cosmetics such as, for example eye shadows, nail varnishes, make-ups, lipsticks, mascara, and also of candles, lamp oils, joss sticks, insecticides, repellents, propellants. The advantage of using the mixtures according to the invention or the compounds of the formula (I) is that they are compatible with a multiplicity of ingredients in the consumer products, as for example with surfactants, acids, bases, preservatives and fragrances, meaning that the functions of a multiplicity of ingredients are unaffected. A further advantage lies in the very good biodegradability of the compounds of the formula (I) and in the high stability in consumer products which contain water.

A further advantage of the compounds of formula (I) is that they can be used at very low concentrations. In the mixtures according to the invention, the odour-boosting effect occurs even with a ratio of all components a to all components b of 1:10 to 1:10000. When the mixtures according to the invention or the compounds of the formula (I) are used in consumer products, the positive effects stated occur even at very low concentrations, more particularly if the concentration of the at least one compound of the formula (I), based on the total weight of the consumer product, is 0.0001 to 0.03 wt %.

In a further aspect, therefore, the present invention relates to the use of the mixtures according to the invention or of the compounds of the formula (I) for boosting an odour, more particularly flowery and/or fruity notes.

Compounds of the formula (I) are also suitable for use as fragrances, especially for generating a fruity and/or flowery aroma.

The compounds of the formula (I) can be obtained by conventional synthesis processes of organic chemistry, as described for example in Organikum, Deutscher Verlag der Wissenschaften, 18th edition. The 1-(4-methylcyclohexyl) ethanol used as reactant is available commercially or else may be obtained by hydrogenation of the corresponding acetophenone.

The examples which follow are intended to illustrate the invention in more detail. Unless indicated otherwise, all details are based on the weight. The compounds prepared were purified by means of distillation or preparative liquid chromatography on silica gel.

EXAMPLES

Example 1: 1-(4-methylcyclohexyl)ethyl propionate 142 g (1 mol) of 1-(4-methylcyclohexyl)ethanol, 88.8 g (1.2 mol) of propionic acid and 1.2 g of concentrated sulphuric acid are heated with 400 ml of toluene on a water separator for 3 hours in a 1 L three-necked flask stirring apparatus. The reaction mixture is washed twice with 10% strength sodium carbonate solution and once with 200 g of water, dried and concentrated. The residue which remains is distilled on a 10 cm packed column. This gives 170 g of product having a GC content (sum of the isomers) of 97.5% (yield: 84% of theory).

For analytical investigations, from the crude product, the stereoisomeric compounds of the formula (A) and (B) were separated from one another by means of high-pressure liquid chromatography on a Phenomenex Luna C18 250*10 mm, 5μ, using water/methanol as eluent. The compound of the formula (A) was obtained with a purity of 99.3% and the compound of formula (B) with a purity of 94.2%.

Compound of the formula (A):

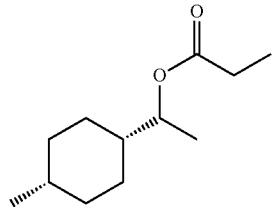

1H NMR (400 MHz, chloroform-d) δ 4.89 (p, J=7.7, 6.3 Hz, 1H), 2.31 (q, J=7.5 Hz, 2H), 1.72 (tt, J=

6.7, 4.1 Hz, 1H), 1.56-1.47 (m, 1H), 1.49-1.40 (m, 2H), 1.46-1.39 (m, 4H), 1.39-1.25 (m, 2H), 1.18

(d, J=6.3 Hz, 3H), 1.14 (t, J=7.6 Hz, 3H), 0.91 (d, J=7.0 Hz, 3H).

13C NMR (101 MHz, CDCl3) δ=174.20, 77.35, 77.03, 76.71, 72.75, 41.22, 30.88, 30.82, 29.04, 28.00, 24.37, 23.95, 19.24, 17.74, 9.30, −0.00.

Compound of the formula (B):

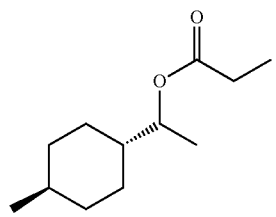

1H NMR (400 MHz, chloroform-d) δ 4.73 (p, J=6.4 Hz, 1H), 2.35-2.25 (m, 2H), 1.80-1.72 (m, 1H), 1.76-1.67 (m, 2H), 1.65 (dt, J=5.6, 3.2 Hz, 1H), 1.38 (dddp, J=14.9, 12.8, 6.4, 3.2 Hz, 1H), 1.27

(dddd, J=16.3, 9.9, 5.7, 2.5 Hz, 1H), 1.18-1.14 (m, 3H), 1.13 (d, J=7.6 Hz, 3H), 1.01 (dddd, J=24.3, 14.9, 12.3, 2.8 Hz, 2H), 0.97-0.87 (m, 2H), 0.87 (d, J=6.5 Hz, 3H).

13C NMR (101 MHz, CDCl3) δ=174.18, 77.33, 77.02, 76.70, 74.40, 42.34, 34.81, 34.76, 32.64, 28.45, 28.39, 27.98, 22.59, 17.25, 9.29, 0.00.

Example 2: 1-(4-methylcyclohexyl)ethyl butyrate 29.8 g (0.21 mol) of 1-(4-methylcyclohexyl)ethanol, 103 g (0.65 mol) of butyric anhydride, 2.35 g (0.02 mol) of 4-dimethylaminopyridine and 0.67 g (0.008 mol) of pyridine are stirred at 120° C. for 2 hours in a 250 ml three-necked flask stirring apparatus. The crude product is introduced into ice-cold 5% strength hydrochloric acid. Extraction with tert-butyl methyl ether, washing to neutrality and drying are followed by concentration on a rotary evaporator. The product is then distilled on a 10 cm packed column. This gives 32.6 g of product having a GC content (sum of the isomers) of 98.8% (yield: 73% of theory).

Example 3: 1-(4-methylcyclohexyl)ethyl 2-methylpropionate 50.0 g (0.35 mol) of 1-(4-methylcyclohexyl)ethanol, 37.2 g (0.42 mol) of 2-methylpropionic acid and 0.5 g of p-toluenesulphonic acid are heated with 100 ml of toluene for 4 hours in a water separator in a 250 ml three-necked flask stirring apparatus. Washing and concentration on a rotary evaporator are followed by distillation on a 10 cm packed column. This gives 30 g of product having a GC content (sum of the isomers) of 98% (yield: 40% of theory).

Example 4: 1-(4-methylcyclohexyl)ethyl 2-hydroxypropionate 40.0 g (0.28 mol) of 1-(4-methylcyclohexyl)ethanol, 28.0 g (0.28 mol) of lactic acid and 2.8 g of p-toluenesulphonic acid are heated under reflux with 100 ml of toluene for 2 hours in a 250 ml three-necked flask stirring apparatus. The crude product is washed to neutrality with sodium hydrogen carbonate solution and water, dried and concentrated on a rotary evaporator. Distillation on 10 cm packed column gives 33.8 g of product having a GC content (sum of the isomers) of 97% (yield: 55% of theory).

Example 5: 1-[1-(ethoxymethoxy)ethyl]-4-methylcyclohexane 35.5 g (0.25 mol) of 1-(4-methylcyclohexyl)ethanol, 130 g (1.25 mol) of formaldehyde diethyl acetal, 1 g of Lewatit K2641 and 100 g of n-hexane are stirred at 74° C. for 10 hours. During the reaction time, 54 g of a mixture of ethanol and n-hexane are removed by distillation. After the end of the reaction, the Lewatit is removed by filtration.

The filtrate is concentrated and then distilled on a 10 cm packed column. This gives 29.1 g of product having a GC content (sum of the isomers) of 97% (yield: 58% of theory).

Example 6: 1-methyl-4-[1-(3-methylbut-2-enoxy)ethyl]cyclohexane 7.5 g of sodium hydride, 250 g of toluene and 17.8 g (0.125 mol) of 1-(4-methylcyclohexyl)ethanol are heated at 100° C. for 1 hour (end of evolution of hydrogen). Thereafter 30 g (0.25 mol) of prenyl chloride are metered in and stirring is continued at 100° C. for 2 hours. After the end of the reaction, the reaction mixture is poured into ice-water, tert-butyl methyl ether is added, and the phases are separated. The organic phase is washed with sodium chloride solution and water, dried and concentrated. The product is distilled on a 10 cm packed column. This gives 20.7 g of product having a GC content (sum of the isomers) of 95% (yield: 75% of theory).

Example 7: Production of a Perfume Oil Having a Flowery-Fruity-Green-Woody Note

The following odorants are mixed in the stated amounts (parts by weight):

| | |
|---|---|
| ACETOACETIC ACID ETHYL ESTER | 6 |
| CITROXAL 50% IN BB 10% DPG | 4 |
| HEXENOL CIS-3 | 1 |
| HEXENYL ACETATE CIS-3 10% DPG | 7 |
| ALLYL AMYL GLYCOLATE | 1 |
| GALBEX TYPE BASE | 10 |
| LINALYL ACETATE | 20 |
| CITRAL FF | 1.5 |
| ORANGE OIL BRAZ. | 9 |
| ALDEHYDE C14 SOG | 6 |
| MALTOL | 1.5 |
| LILIAL REPLACER BODYWASH 2 | 8 |
| HELIONAL | 15 |
| FLOROSA BM/PYRANOL | 40 |
| TETRAHYDROLINALOOL | 20 |
| PHENYLETHYL ALCOHOL | 70 |
| CITRONELLOL 950 | 9 |
| NEROL 900 | 15 |
| ROSAPHEN ® | 20 |
| DAMASCONE DELTA 10% DPG | 8 |
| BENZYL ACETATE | 12 |
| HEDIONE | 280 |
| JASMONE CIS | 1 |
| VELOUTONE 10% DPG | 3 |
| AMYL SALICYLATE N | 4 |
| HEXENYL SALICYLATE CIS-3 | 12 |
| HEXYL SALICYLATE | 25 |
| ISORALDEINE 70 | 12 |
| COUMARIN 10% DPG | 5 |
| ISO E SUPER | 120 |
| TRIMOFIX O | 8 |
| VETIVAL ® | 3 |
| VETIVERYLIA BASE | 5 |
| ISOBORNYLCYCLOHEXANOL | 40 |
| SANDRANOL ® | 25 |
| EVERNYL | 3 |
| DIPROPYLENE GLYCOL | 170 |
| Total | 1000 |

In a shower gel, using the stated odorant composition, after addition of 40 parts by weight of 1-(4-methylcyclohexyl)ethyl propionate (compound 1) and corresponding reduction by 40 parts by weight of the dipropylene glycol solvent, the soft flowery and fruity note is boosted and rounded out. Furthermore, a citronellol-like rose odour is generated.

The perfume oils and a solution of compound 1 are each applied to a scent strip and subjected to sensorial testing. In this testing, the odour intensity of the floweriness and of the fruitiness are evaluated sensorially on a scale from 0 (no fruitiness or floweriness) to 10 (very strong floweriness or fruitiness). The results are set out in the table below.

| Example No. | Odour intensity of floweriness | Odour intensity of fruitiness |
| --- | --- | --- |
| 7 without compound 1 | 4 | 2 |
| Solution of compound 1* | 3 | 3 |
| 7 with compound 1 | 9 | 8 |

*40 parts by weight of compound 1 in solution in 960 parts by weight of the virtually odourless solvent dipropylene glycol

Example 8: Production of a Perfume Oil Having a Flowery-Fruity-Rosy Wood Note The following odorants are mixed in the stated quantities (parts by weight):

| | |
| --- | --- |
| HEXENYL ACETATE CIS, TRANS-3 10% DPG | 4 |
| VERTOCITRAL | 0.5 |
| MAGNOLAN | 20 |
| LINALYL ACETATE | 25 |
| LEMON OIL WINTER ITALY | 10 |
| MANDARIN OIL ITAL. | 5 |
| RED BERRIES EXTRACT 10% DPG | 2 |
| CASSIS 345B TYPE BASE W/O MYRCENE | 8 |
| HELIONAL | 4 |
| FLOROSA | 15 |
| LINALOOL | 5 |
| PHENYLETHYL ALCOHOL | 20 |
| CITRONELLOL 950 | 10 |
| GERANIOL 60 | 20 |
| DAMASCENONE TOTAL 10% DPG | 5 |
| DAMASCONE ALPHA 10% DPG | 1 |
| ROSE DE MAI-BASE | 8 |
| HEDIONE | 140 |
| HEXYLCINNAMALDEHYDE ALPHA | 20 |
| METHYL OCTINE CARBONATE 1% DPG | 5 |
| IONONE BETA | 8 |
| TABANONE 1% DPG | 5 |
| CEDAR WOOD OIL VIRGINIA | 1.5 |
| AMBERWOOD ® F | 5 |
| TIMBERSILK | 100 |
| VETIKOLACETAT ® | 0.5 |
| AMBRA CORE | 3 |
| AMBROXIDE | 7 |
| AMBRETTOLIDE | 2 |
| GALAXOLIDE 50% IN IPM | 400 |
| INDOL FF 10% DPG | 1 |
| DIPROPYLENE GLYCOL | 139.5 |
| Total | 1000 |

The addition of 20 parts by weight of 1-(4-methylcyclohexyl)ethyl propionate (from example 1) and corresponding reduction by 20 parts by weight of dipropylene glycol solvent produces, in an eau de toilette (EDT), an interesting peony note, which emphasizes naturalness and boosts the fruitiness.

Example 9

The odorant composition indicated in example 8, including the added 20 parts by weight of 1-(4-methylcyclohexyl) ethyl propionate (from example 1), is incorporated at a concentration of 1 wt % into a shower gel and subjected to a stability test (4 weeks of storage at 40° C.), with no loss occurring in the intensity of the peony note, the naturalness and the fruitiness.

Example 10: Production of a Perfume Oil Having a Flowery-Fruity-Green-Woody Note The following odorants are mixed in the stated quantities (parts by weight):

| | |
| --- | --- |
| ACETOACETIC ACID ETHYL ESTER | 7 |
| HEXENOL CIS-3 | 1 |
| HEXENYL ACETATE CIS-3 10% DPG | 7 |
| ALLYL AMYL GLYCOLATE | 1 |
| GALBEX TYPE BASE | 10 |
| BERGAMOT OIL BERGAPTENE-FREE | 20 |
| LEMON OIL ITAL. | 20 |
| ORANGE OIL BRAZ. | 12 |
| ALDEHYDE C14 SOG | 6 |
| CASSIS 345B TYPE BASE | 3 |
| MALTOL | 1 |
| HELIONAL | 15 |
| FLOROSA BM/PYRANOL | 38 |
| HYDROXYCITRONELLAL | 28 |
| GERANIUM OIL BOURBON 10% DPG | 3 |
| PHENYLETHYL ALCOHOL | 70 |
| DAMASCENONE 10% DPG | 3 |
| BENZYL ACETATE | 12 |
| HEDIONE | 155 |
| HEDIONE HC/30 | 185 |
| JASMONE CIS | 1 |
| VELOUTONE 10% DPG | 2 |
| HEXENYL SALICYLATE CIS-3 | 33 |
| ISORALDEINE 95 | 17 |
| ETHYLVANILLIN 10% DPG | 0.5 |
| COUMARIN 10% DPG | 5 |
| ISO E SUPER NON DISCOLORING | 180 |
| TRIMOFIX O | 15 |
| ISOBORNYLCYCLOHEXANOL | 60 |
| SANDRANOL ® | 40 |
| EVERNYL | 3 |
| AMBRETTOLIDE | 5 |
| EXALTENONE 942008 | 1.5 |
| GALAXOLIDE 50% IN IPM | 30 |
| DIPROPYLENE GLYCOL | 10 |
| Total | 1000 |

The addition of 10 parts by weight of 1-(4-methylcyclohexyl)ethyl propionate (from example 1) and corresponding reduction by 10 parts by weight of dipropylene glycol solvent endows an eau de toilette (EDT) with more liveliness, volume, floweriness and fruitiness.

What is claimed is:
1. A mixture comprising:
at least one fragrance of the formula (I)

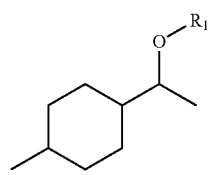

Formula (1)

where
$R_1$=OC—$R_2$, $CH_2OR_3$, $C_1$-$C_8$ open-chain or branched aliphatic radical, optionally substituted and/or unsaturated,
with $R_2$=an open-chain or branched aliphatic radical, optionally substituted and/or unsaturated, having 2-10 C atoms,
with $R_3$=an open-chain or branched aliphatic radical, optionally substituted and/or unsaturated, having 1-8 C atoms; and at least one second fragrance, where the at least one second fragrance is different from the at least one fragrance of the formula (I);

wherein the weight ratio of the at least one fragrance of the formula (I) to the at least one second fragrance is from 1:20.75 to 1:10000.

2. The mixture according to claim 1, wherein R₁ is a propanoyl, butanoyl, 2-methylpropanoyl, 2-hydroxypropanoyl, methoxyethyl or 2-methylbut-2-enyl radical.

3. The mixture according to claim 1, wherein the at least one fragrance of the formula (I) is selected from 1-(4-methylcyclo-hexyl)ethyl propionate, 1-(4-methylcyclohexyl)ethyl butyrate, 1-(4-methylcyclo-hexyl)ethyl isobutyrate, 1-(4-methylcyclo-hexyl)ethyl 2-hydroxypropionate, 1-[1-ethoxy-methoxy]ethyl]-4-methyl cyclohexane and 1-methyl-4-[1-(3-methylbut-2-enoxy)ethyl]cyclohexane.

4. The mixture of claim 1, wherein the at least one fragrance of the formula (I) is at least two fragrances of the formula (I).

5. The mixture according to claim 1, wherein the weight ratio of the at least one fragrance of the formula (I) to the at least one second fragrance is from 1:49.25 to 1:10000.

6. The mixture according to claim 1, wherein the at least one fragrance of the formula (I) is a fragrance have the following formula:

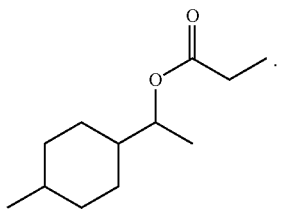

7. A compound comprising one of the following formulas:

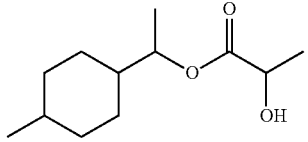

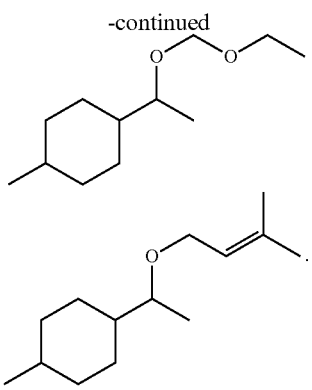

8. A fragrance, for boosting flowery and fruity odour impressions, comprising a mixture according to claim 7.

9. A consumer product comprising a compound according to claim 7.

10. A consumer product comprising a mixture according to claim 1.

11. A consumer product according to claim 10, comprising water.

12. A consumer product according to claim 11, wherein the fraction of water in the consumer product is 5.0 to 99.0 wt %.

13. A fragrance, for boosting flowery and fruity odor impressions, comprising a compound according to claim 1.

14. A compound comprising the following formula:

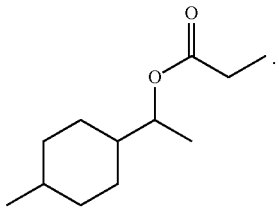

15. The compound of claim 14, wherein the compound has a rose odor.

16. A consumer product comprising a compound according to claim 14.

17. A fragrance, for boosting flowery and fruity odour impressions, comprising a mixture according to claim 14.

* * * * *

UNITED STATES PATENT AND TRADEMARK OFFICE
CERTIFICATE OF CORRECTION

PATENT NO. : 10,415,001 B2
APPLICATION NO. : 15/197199
DATED : September 17, 2019
INVENTOR(S) : Erich Dilk et al.

It is certified that error appears in the above-identified patent and that said Letters Patent is hereby corrected as shown below:

Column 15, Line 23, Claim 5:
After "second fragrance is from"
Delete "1:49.25" and
Insert -- 1:43.025 --.

Signed and Sealed this
Seventh Day of April, 2020

Andrei Iancu
*Director of the United States Patent and Trademark Office*